United States Patent [19]

Muller

[11] Patent Number: 5,425,762
[45] Date of Patent: Jun. 20, 1995

[54] PROSTHETIC IMPLANTS AND PROCESS FOR OBTAINING THE SAME

[76] Inventor: Guy-Henri Muller, 45 rue Goethe 6700, Strasbourg, France

[21] Appl. No.: 69,762

[22] Filed: Jun. 1, 1993

[51] Int. Cl.$^6$ ............................ A61F 2/02; A61F 2/12
[52] U.S. Cl. ......................................... 623/11; 623/7; 623/8
[58] Field of Search .................. 623/7, 8, 11, 6, 66

[56] References Cited

U.S. PATENT DOCUMENTS

| | | | |
|---|---|---|---|
| 4,138,382 | 2/1979 | Polmanteer | 623/7 X |
| 4,157,085 | 6/1979 | Austad . | |
| 5,074,878 | 12/1991 | Bark et al. | 623/8 |
| 5,118,371 | 5/1992 | Christensen et al. | 623/8 X |
| 5,213,579 | 5/1993 | Yamada et al. | 623/11 X |
| 5,219,360 | 6/1993 | Georgiade | 623/8 |

FOREIGN PATENT DOCUMENTS 2047101 11/1980 United Kingdom .

OTHER PUBLICATIONS

Yasuo Mutou, "Augmentation Mammaplasty with the Akiyama Prosthesis," *British J. Plastic Surgery*, 23, pp. 58–62 (1970).
V. Stoy & C. Kliment, "Hydrogels: Specialty Plastics for Biomedical and Pharmaceutical Applications," Advance Sheet for Presentation of May 29–30, 1991 at Hotel International, Basel, Switzerland.

*Primary Examiner*—Mary Beth O. Jones
*Attorney, Agent, or Firm*—Fulwider Patton Lee & Utecht

[57] ABSTRACT

A surgically implantable prosthetic device wherein dry particles of hydrogel/silicone combinations are contained within an envelope. The dry character of the device allows it to be sterilized without adverse affect, while injection of water or physiological fluid after implantation causes it to swell to proper size and texture.

8 Claims, No Drawings

PROSTHETIC IMPLANTS AND PROCESS FOR OBTAINING THE SAME

This invention relates to prosthetic implants and specifically to mammary implants which are largely used in plastic, aesthetic and reparative surgery to repair irregularities of parts of the human body by modifying the part volume and/or improving the contours thereof.

Such implants have been developped during the last 10 years and an interesting modification is described in U.S. patent application Ser. No. 07/339,713. In this modification is described a mammary implant comprising a silicone thin envelope filled by a number of small individual closed capsules also comprising a silicone thin membrane and filled with a physiological salt solution.

However such implants have a limited use, due to the need of a sterilization of the capsules, by thermal treatment or by irradiation, which can lead to a rupture of the membrane under the thermal expansion of the solution.

This invention avoids this limitation by replacing such individual capsules filled with a liquid by individual dry material particles having each the property to absorb liquids such as water or physiological solutions and to swell until forming a flexible individual particle having a gel consistency and a volume of several times the volume of the original dry particle.

Such flexible particles comprising no membrane, the prior limitation is therefore eliminated, since they can expand to any degree without any chance of rupture.

There are a number of materials having the property to absorb liquids and to swell at different degrees. The invention resides in the selection of the material which is the most appropriate for this new application.

The materials used in this invention comprise the associations of silicones with hydrogels.

Hydrogels as such are well known for other applications, i.e. as water retainers and—carriers for agricultural purposes, and as water absorbers in health articles such as diapers and the same.

However they cannot be used as such for the present application since, due to their chemical structure, they would coalesce when swollen, giving an unique rigid mass.

To prevent such drawback, said hydrogels are associated with a silicone elastomer to obtain dry granules which are used to fill the implant external envelope, which allows the entire implant to be sterilized in the usual ways. The dry sterilized implants is then put in place in the patient's body and finally water or a physiological salt solution is injected into the implant to initiate the swelling of the individual particles until a given volume is reached.

By "hydrogel/silicone association" different possibilities are covered by this invention.

According a first modification dry silicone granules are coated with an hydrogel according to a process which has been described for building intravascular catheters (Vladimir STOY & Charles KLIMENT in "Hydrogels: Speciality Plastics for Biomedical and Pharmaceutical Applications".

In a second modification, dry porous silicone granules or spherules are impregnated with an hydrogel according to a capillarity process. In this specific case, when placed in contact with water, each of such impregnated granules is swelling as a whole; thereafter the hydrogel can be expelled from the swollen granule by compression of the same but can return into said granules when releasing the pressure.

In a third modification, which is preferred in this invention, the hydrogel/silicone association is of chemical nature, i.e. the material used as dry particles is an hydrogel/polysiloxane copolymer.

In this specific modification, there can be used as an hydrogel component of the copolymer either a biodegradable hydrogel or a non-biodegradable copolymer.

If a biodegradable hydrogel is used, it is destroyed in case of implant breakage or rupture and it is clear that the products resulting from this destruction should not be toxic.

If a non-biodegradable hydrogel is used, it is permanently tied with the silicone elastomer and it can be extracted during the intervention which follows in case of a breakage of the implant.

In most cases, the hydrogel characteristics are between both extremes.

The copolymers used in this invention are therefore hybrid hydrogels which can be subdivided into small dry particles or micro spheres which are used to fill the usual envelope made of a thin silicone film adapted for building an implant such as a mammary implant.

Such particles being dry, they can be sterilized by the usual methods and apparatus without being impaired by any treatment. The above drawback is therefore completely eliminated.

When the envelope is filled with the requested amount of such dry particles, it is placed in the patient's body by the usual surgical methods; thereafter, sterile water is injected into the implant by using a needle punched through a safery patch, i.e. a portion of the envelope comprising a film having the property to close itself after having been perforated (self-healing film), which is well known in the art.

The amount of injected water should be slightly more than the amount which can be absorbed by the hydrogel, so that the implant has the requested volume with the maximal hydratation of the hydrogel, depending on the number of the particles and their volume when swollen.

When swollen, the particles do not coalesce but are still independant and slidably movable each with respect to the others. The consequence thereof is that even in case of breakup of this implant external enveloppe, there is no risk of leakage of water out of said envelope. It can happen that some hydrated particles are free out of the envelope in the prosthethic cicatricial area, but then, they can be easily removed by suction during the replacement of the broken implant.

As examples of known hydrogels which can be copolymerized with polysiloxanes to obtain the materials used in the form of dry microparticles of the invention, it can be cited polyacrylamides cross-linked with various monomers as described in Chemical Abstracts 69, N° 17, 1968 and in Chemical Abstracts 74, N° 3, 1971.

Regarding the external envelope or membrane to be filled with said particles to form the implant of the invention, several modifications are possible in the scope of the invention.

According a first modification, the membrane is made of silicone elastomer, which can be smooth or rough. It must comprise a thick portion or patch having self-healing characteristics, which allows the introduction of water or physiological serum by temporarily punching by a needle or by a filling tube equipped with a filling valve. Said needle or said tube are thereafter removed and the material of the patch closes by itself.

According to a second modification, the membrane can be made of a hydrogel/silicone copolymer of the same nature as the particles and which is wholly self-healing. In this specific case the implant is easily placed into the patient's body when dry, then gradually swollen during the post-operative period by random punching of the membrane through the skin.

This modification is of special importance in the cases of immediate re-building after a breast removal.

The implant of the invention avoids two major drawbacks of the known implants:

It eliminates the use of silicone gel, short chains of which can migrate out of the implant towards the peri-prosthetic tissues, which is an important cause of formation of the well known hard peri-prosthetic contractile "capsule".

It prevents any total or partial deflation of the known inflated implants filled with physiological serum even in case of punching through the implant or of breakage of the exernal enveloppe.

It has in addition the advantage that the silicone/hydrogel association, when hydrated, has a stable structure, easy to remove by suction in case of breakage of the envelope.

The individual particles can reach, after swollen, a volume of 1 to 5 cc, which can easily be detected by echography or radiography, specifically when they are out of the envelope, which allows a tracing of any envelope breakage.

It is clear that the mammoplasty is one of the most important applications of the invention, but that the implants of the invention can be adapted to the re-building of different portions of the human body, such as calves, chin, scalp and the same, with the same advantages.

The same granules of hybrid hydrogels can also be used to repair the ripples on the face. In this case, the dry particles are directly percolated into the ripples, thereafter swollen with water or physiological serum through the skin which is then the external envelope itself.

I claim:

1. A surgically implantable prosthesis, comprising:
   an envelope; and
   a plurality of individual dry particles contained within said envelope wherein each particle consists of a hydrogel intimately associated with silicone whereby injection of a water or physiological fluid into said envelope causes said particles to swell.

2. The surgically implantable prosthesis of claim 1, characterized in that each dry particle is a granule of silicone coated with said hydrogel.

3. Implant according to claim 1, characterized in that each dry particle is a porous microsphere of silicone impregnated with said hydrogel.

4. Implant according to claim 1, characterized in that each dry particle is a granule of an hybrid hydrogel obtained by copolymerization between said hydrogel and said silicone wherein said silicone is a polysiloxane.

5. The surgically implantable prosthesis of claim 1, characterized in that said hydrogel is biodegradable, its degradation products being non-toxic for the human organism.

6. Implant according to any of claim 4, characterized in that the hydrogel is not biodegradable and as a result of said copolymerization, is bonded to said silicone, wherein said hybrid hydrogel can be removed by suction.

7. The surgically implantable prosthesis of claim 1, characterized in that the envelope is a thin membrane made of silicone elastomer that is self-healing pursuant to being temporarily pierced by a needle for injection of water or physiological serum.

8. The surgically implantable prosthesis of claim 1, characterized in that the external envelope is a self-healing membrane made of a copolymer of hydrogel and silicone.

* * * * *